United States Patent [19]

Mueller et al.

[11] Patent Number: 5,401,486
[45] Date of Patent: Mar. 28, 1995

[54] PREPARATION OF ESSENTIALLY ALKALI-FREE TITANIUM ZEOLITES

[75] Inventors: Ulrich Mueller, Neustadt; Wolfgang Hoelderich, Frankenthal, both of Germany

[73] Assignee: BASF Aktiengesellschaft, Ludwigshafen, Germany

[21] Appl. No.: 164,425

[22] Filed: Dec. 8, 1993

Related U.S. Application Data

[63] Continuation of Ser. No. 969,728, Oct. 30, 1992, abandoned.

[30] Foreign Application Priority Data

Nov. 21, 1991 [DE] Germany .......... 41 38 155.6

[51] Int. Cl.⁶ .......... C01B 33/34
[52] U.S. Cl. .......... 423/705; 423/713; 423/DIG. 22
[58] Field of Search ........ 423/705, 713, 718, DIG. 22

[56] References Cited

U.S. PATENT DOCUMENTS

| | | |
|---|---|---|
| 3,329,681 | 7/1967 | Young et al. |
| 4,410,501 | 10/1983 | Taramasso et al. |
| 4,666,692 | 5/1987 | Taramasso et al. |
| 4,707,345 | 11/1987 | Lok et al. .......... 423/713 |
| 4,859,785 | 8/1989 | Bellussi et al. .......... 549/531 |
| 4,869,805 | 9/1989 | Lok et al. .......... 208/111 |
| 5,082,641 | 1/1992 | Pope et al. |
| 5,098,687 | 3/1992 | Skeels et al. .......... 423/DIG. 22 |
| 5,160,717 | 11/1992 | Lok et al. .......... 423/704 |
| 5,254,766 | 10/1993 | Costantini et al. .......... 502/232 |
| 5,332,830 | 7/1994 | von Locquenghien et al. .......... 548/262.2 |

FOREIGN PATENT DOCUMENTS

| | | |
|---|---|---|
| 0132550 | 2/1985 | European Pat. Off. .... 423/DIG. 22 |
| 0200260 | 12/1986 | European Pat. Off. |
| 0208311 | 1/1987 | European Pat. Off. |
| 0266825 | 10/1987 | European Pat. Off. |
| 0267362 | 5/1988 | European Pat. Off. |
| 0311983 | 4/1989 | European Pat. Off. |
| 0376453 | 7/1990 | European Pat. Off. |
| 2089069 | 6/1982 | United Kingdom . |
| 2116974 | 10/1983 | United Kingdom . |
| 8504853 | 11/1985 | WIPO . |

OTHER PUBLICATIONS

Notari, Studies in Surface Science and Catalysis, vol. 37, pp. 413–425 (1987) Sep.
J. Chem. Soc., Chem. Commun., 678–680 (1991) (no month) Behrens et al.

*Primary Examiner*—Mark L. Bell
*Assistant Examiner*—David Sample
*Attorney, Agent, or Firm*—John H. Shurtleff

[57] ABSTRACT

A process for preparing essentially alkali-free titanium silicate crystals having a zeolite structure, comprises reacting an $SiO_2$-containing mixture of water, a tetraalkylammonium compound, a titanium component and ammonia in the absence of a metal hydroxide or salt under hydrothermal conditions in a molar ratio of ammonia/tetraalkylammonium of from 3:1 to 200:1.

8 Claims, No Drawings

PREPARATION OF ESSENTIALLY ALKALI-FREE TITANIUM ZEOLITES

This application is a continuation of application Ser. No. 07/969,728, filed Oct. 30, 1992 (abandoned).

The present invention relates to a process for preparing essentially alkali-free titanium silicate crystals having a zeolite structure in the absence of a metal hydroxide or salt under hydrothermal conditions.

BACKGROUND OF THE INVENTION

Zeolites are, as will be known, crystalline alumosilicates having ordered channel and cage structures, whose pore openings are in the micropore region of less than 0.9 nm. The network of such zeolites is composed of $SiO_4$ and $AlO_4$ tetrahedra joined together via common oxygen bridges. A survey of the known structures may be found for example in W. M. Meier and D. H. Olson, Atlas of Zeolite Structure Types, 2nd edition, Butterworths, London 1987.

To balance out the negative electrovalence due to the incorporation of Al(III) into the Si(IV) silicate lattice, zeolites are found to contain exchangeable cations, in particular, depending on the method of preparation, cations of sodium, potassium, lithium or cesium. Replacing these cations for protons, for example by ion exchange, gives the corresponding acidic solids with the zeolite structure in the H-form.

U.S. Pat. No. 3,329,481 discloses materials in which the Si(IV) in the silicate lattice is said to be replaced by titanium in the form of Ti(IV). These titanium zeolites, in particular those having a crystal structure of the MFI type (cf. Meier, Olson, loc. cit.), and methods for preparing them are described for example in U.S. Pat. No. 4,410,501, EP-A-311,983, U.S. Pat. No. 4,666,692, DE-A-30 47 798 or BE-A-10 01 038. Titanium-containing zeolites having other structures are known from EP-A-405,978. Apart from silicon and titanium, these materials may also contain additional elements such as aluminum (DE-A-31 41 238), gallium (EP-A-266,825), boron (U.S. Pat. No. 4,666,692) or small amounts of fluorine (EP-A-292,363).

Titaniumzeolites with an MFI structure are known to be identifiable from a certain pattern in their X-ray diffractograms and also from a structural vibration band in the IR region at about 950 $cm^{-1}$ (DE-A-30 47 798) and hence to be distinguishable from alkali metal titanates or crystalline and amorphous $TiO_2$ phases.

Titanium zeolites with an MFI structure are known to be suitable for use as catalysts for oxidation reactions (B. Notari, Stnd. Surf. Sci. Catal., 37 (1987), 413–425). For instance, EP-A-100,118 discloses a process whereby propene can be epoxidated with hydrogen peroxide in aqueous phase to propylene oxide over titanium zeolites. The preparation of cyclohexanone oxime from cyclohexanone by reaction with ammonia and hydrogen peroxide is taught in EP-A-208,311 and the hydroxylation of aromatics is known from GB-A-21 16 974. The oxidation of saturated hydrocarbons from $C_2$ to $C_{18}$ with $H_2O_2$ over the abovementioned titanium zeolites is described in EP-A-376,453.

The aforementioned titanium zeolites are typically prepared by reacting an aqueous mixture of an $SiO_2$ source, a titanium dioxide and a nitrogen-containing organic base, for example tetrapropylammonium hydroxide, in a pressure vessel at elevated temperature over a period of several hours or a few days in the absence or presence of alkali. The crystalline product is filtered off, washed and dried and then calcined at elevated temperature to remove the organic nitrogen base. In the powder thus obtained at least some of the titanium is present within the zeolite structure in varying proportions with four-, five- or six-fold coordination (Behrens et all, J. Chem. Soc., Chem. Commun. 1991, 678–680). To improve the catalytic properties, the titanium zeolite powder may additionally be subjected to a repeated wash with a hydrogen peroxide solution acidified with sulfuric acid, after which the titanium zeolite powder must be dried and calcined again, for example as described in EP-A-267,362. The pulverulent titanium zeolite must then be finally processed in a shaping operation with additions of suitable inert binder to obtain a handleable catalyst. A method for this is described in EP-A-200,260.

Existing methods for preparing titanium zeolites with an MFI structure have some serious disadvantages. For instance, tetrapropylammoniumhydroxide TPAOH that contains only a small residue of alkali metal, in particular potassium, is a very costly starting material which must be used in high concentrations. The processing of the titanium zeolite powder prepared by means of the TPAOH by shaping to fabricate handleable catalysts is labor intensive and after an extrusion with or without an inert binder requires a further energy and time intensive drying and calcining step.

SUMMARY OF THE INVENTION

It is an object of the present invention to remedy the aforementioned disadvantages.

We have found that this object is achieved by a novel and improved process for preparing essentially alkali-free titanium silicate crystals having a zeolite structure, which comprises reacting an $SiO_2$-containing mixture of water, a tetraalkylammonium compound, a titanium component and ammonia in the absence of a metal hydroxide or salt under hydrothermal conditions in a molar ratio of ammonia/tetraalkylammonium of from 3:1 to 200:1.

DETAILED DESCRIPTION OF THE INVENTION

The process of the invention makes it possible to obtain crystals of titanium silicates having a zeolite structure by hydrothermal reaction of an $SiO_2$ source with a titanium Component in the presence of aqueous solutions of weakly concentrated tetraalkylammonium halides and ammonia. Specifically, the process of the invention gives the titanium zeolite crystals in a high yield directly in the form of plateletlike, very substantially alkali-free, large primary crystallites which, owing to their particle size, can be used without further molding steps as catalysts for reacting organic molecules, specifically in fluidized bed, trickle bed or suspension processes.

Examples of suitable tetrapropylammonium halides (TPAHs) are tetrapropylammonium fluoride, tetrapropylammonium chloride, and tetrapropylammonium bromide, of which tetrapropylammoniumbromide is preferred. The molar ratio of TPAH/$SiO_2$ is from 0.042:1 to 0.2:1, preferably from 0.05:1 to 0.15:1. It is advantageous to carry out the crystallization of the titanium silicates with the zeolite structure hydrothermally at from 100° to 250° C., in particular at from 120° to 200° C., especially at from 150° to 190° C. It is advisable to maintain for the reaction a molar ratio of ammonia, used as aqueous solution, to $SiO_2$ of from 10:1 to 1:1, preferably from 6:1 to 1.5:1, particularly preferably from 5:1 to 3:1.

The process of the invention produces catalytically usable titanium silicate zeolites by adding the titanium component to the hydrothermal reaction mixture in the form of a soluble, aqueous or aqueous/alcoholic peroxotitanate compound in the aforedescribed manner. This is possible by employing $SiO_2/TiO_2$ in a molar ratio of from 10:1 to 1500:1, preferably from 10:1 to 250:1, particularly preferably from 10:1 to 100:1, and/or a dilution of $SiO_2/H_2O$ of from 0.07:1 to 0.025:1, preferably from 0.05:1 to 0.04:1.

The alkali-free process of the invention makes it possible, furthermore, that, following a heat treatment at from 350° to 600° C., preferably at from 400° to 550° C., particularly preferably at from 450° to 500° C., the material is present directly and without additional ion exchange and in particular, on account of the crystal size of from 1 to 50 μm, preferably from 3 to 30 μm, and the plateletlike crystal form, in a catalytically effective form without further shaping and can be used directly as a catalyst.

The amine-free titanium silicates with an MFI structure prepared according to the invention have a characteristic band in their IR spectrum at from 950 to 960 $cm^{-1}$, whereas the titanium silicates which still contain the tetrapropylammonium but are otherwise prepared according to the invention possess this band only following a heat treatment at from 350° to 600° C., in particular at from 450° to 550° C. Characterization of the titanium silicates is also possible from their specific X-ray diffractogram in that the essentially amine-free titanium silicates, i.e. those which contain from 0 to 500 ppm, preferably from 0.001 to 200 ppm, particularly preferably from 0.01 to 50 ppm, of basic (amine-containing) components, have a diffractogram corresponding to the orthorhombic MFI structure.

The titanium silicate zeolites preparable by the present process can be used for the catalytic interconversion of organic molecules. Examples of reactions of this kind are oxidations, the epoxidation of olefins such as propylene oxide from propylene and $H_2O_2$, the hydroxylation of aromatics such as hydroquinone from phenol and $H_2O_2$, the conversion of alkanes to alcohols, aldehydes and acids, isomerization reactions such as the conversion of epoxides into aldehydes and further reactions with such catalysts described in the literature, for example in W. Hölderich, Zeolites: Catalysts for the synthesis of organic compounds, Elsevier, Stud. Surf. Sci. Catal. 49 (1989), 69–93, in particular for the possible oxidation reactions by B. Notari in Stud. Surf. Sci. Catal. 37 (1987), 413–425.

The special pore structure of the material and its simple preparation make it possible for the titanium silicate zeolites preparable according to the invention to be used as microporous adsorbents, for example for removing organic molecules or isomers thereof in liquid or gaseous phase.

The examples which follow will illustrate the manufacturing process of the invention and the catalytic properties of the resulting titanium silicates with an MFI structure.

EXAMPLES

Example 1

This Comparative Example describes the preparation of a titanium silicate with MFI structure in accordance with the state of the art as represented in EP-A-376,453.

30 ml of tetraethyl orthotitanate (Aldrich Chemical Company) were added dropwise with stirring (300 rpm) over 15 minutes to 375 ml of deionized water previously cooled down to 2° C. Then 360 ml of a cold hydrogen peroxide solution (30% by weight) were added to form a reddish orange solution, which was stirred for 2 hours. Then 625 ml of an aqueous tetrapropylammonium hydroxide solution (20% by weight, Fluka) were added, followed after an hour by 100 g of a colloidal silicasol solution (40% by weight of $SiO_2$, Ludox AS-40, Du Pont). This mixture was stored overnight at room temperature, boiled the next day at 80° C. with stirring (300 rpm) for 7 hours, introduced into a 2 l capacity stirred pressure vessel and reacted at 175° C. for 240 hours.

The cold reaction mixture was filtered, the filter cake was repeatedly washed neutral with deionized water, dried overnight at 120° C. and then calcined at 550° C. in air.

Based on starting $SiO_2$, the yield of titanium zeolite was 93%. According to the X-ray diffraction pattern, it is a pure titanium zeolite of the silicalite type.

Example 2

This Synthesis Example describes the novel effect obtained on switching from tetrapropylammonium hydroxide to tetrapropylammonium bromide while at the same time using ammonia solution.

In a glass flask equipped with a stirrer and a reflux condenser, 45.1 g of deionized water are cooled down to 5° C. 6.9 g of tetraisopropyl orthotitanate and 81.4 g of hydrogen peroxide solution (30% by weight) are added dropwise in the course of 15 minutes. To the resulting reddish orange solution is added 211.0 g of an ammonia solution (25% by weight), and the resulting batch is left to warm up overnight to room temperature. Finally, it is heated over 3 hours to 80° C. with stirring. Any weight loss is compensated by addition of a corresponding amount of ammonia solution.

Of this solution thus prepared, 156.8 g are mixed with 56 g of tetrapropylammonium hydroxide solution (20% in water) and 52.8 g of Ludox AS-40 silicasol (Du Pont) in the course of 3 minutes, and the mixture is introduced into a Teflon-lined autoclave vessel and sealed pressuretight. This batch will hereinafter be referred to as batch A.

A further 156.5 g of the solution prepared at the beginning are mixed with 14.7 g of tetrapropylammonium bromide in 44.8 g of water and 53.1 g of Ludox AS-40 silicasol (Du Pont) in the course of 3 minutes, and the mixture is introduced into a Teflon-lined autoclave vessel and sealed pressuretight. This batch will hereinafter be referred to as batch B.

Batches A and B are reacted separately from each other at from 183 to 185° C. over 192 hours. The crystalline reaction products are filtered off, washed neutral, dried and calcined in air at 500° C. in the course of 5 hours.

The properties of the two batches are compared below in Table 2.

TABLE 2

| Batch | Yield | Si/Ti molar | Potassium % by weight | Size μm | Shape |
|---|---|---|---|---|---|
| A | 96% | 36 | 0.89 | 5 | globular |
| B | 95% | 36 | 0.0012 | 26 | plateletlike |

The different habits of the crystals of batches A and B are clearly discernible. The crystallites of batch A, prepared using the costly tetrapropylammonium hydroxide, are intergrown and rather globular in shape, while the crystals of batch B, crystallized with tetrapropylammonium bromide, are very uniform in size and differ in their elongate plateletlike appearance distinctly from batch A in respect of shape and size.

The crystals prepared with tetrapropylammonium hydroxide (batch A) contain a very much higher level of the contaminant potassium compared with the titanium silicates of batch B, synthesized according to the invention using small amounts of tetrapropylammonium bromide.

Example 3

Describes the synthesis process of the invention as practised on an enlarged stirred reaction batch.

In a glass flask equipped with a stirrer and a reflux condenser, 112.5 g of deionized water are cooled down to 5° C. 34.7 g of tetraisopropyl orthotitanate and 203.6 g of a hydrogen peroxide solution (30% by weight) are added dropwise over 15 minutes. To the resulting reddish orange solution is added 527.5 g of an ammonia solution (25% by weight) and the resulting batch is left overnight to warm to room temperature. It is finally heated with stirring to 80° C. over 3 hours. Any weight loss is made good by adding a corresponding amount of ammonia solution. The solution thus prepared is introduced into a stirred steel autoclave together with 73.5 g of tetrapropylammonium bromide, 224.8 g of water and 264.1 g of Ludox AS-40 silicasol.

The reaction mixture is stirred at 185° C. at 100 rpm for 168 hours and then cooled down, and the crystalline product is filtered off, washed neutral, dried and calcined in air at 500° C. in the course of 5 hours.

The product shows the typical X-ray diffractogram of TS-1 titanium silicalite. The crystals are from 2 to 25 μm in size and have a plateletlike habit. The IR recording shows a distinct sharp band at 955 cm$^{-1}$. Chemical analysis reveals a molar ratio in the product of Si/Ti=16.6. Based on starting SiO$_2$, the yield of crystalline, calcined product was 96.3%.

Example 4

Describes the synthesis process of the invention using pyrogenic silica as SiO$_2$ source.

In a glass flask equipped with a stirrer and a reflux condenser, 45.2 g of deionized water are cooled down to 5° C. 6.9 g of tetraisopropyl orthotitanate and 81.5 g of hydrogen peroxide solution (30% by weight) are added dropwise in the course of 15 minutes. To the resulting reddish orange solution is added 211.0 g of an ammonia solution (25% by weight), and the resulting batch is left to warm up overnight to room temperature. Finally, it is heated over 3 hours to 80° C. with stirring. Any weight loss is compensated by addition of a corresponding amount of ammonia solution. The solution thus prepared is introduced into a steel autoclave together with 14.7 g of tetrapropylammonium bromide, 75.5 g of water and 22.1 g of Aerosil-200 (Degussa, pyrogenic silica).

The reaction mixture is left at 185° C. for 168 hours and then cooled down, and the crystalline product is filtered off, washed neutral, dried and calcined in air at 500° C. in the course of 5 hours.

The product shows the typical X-ray diffractogram of TS-1 titanium silicalite. The crystals have a uniform size of about 8 μm and a plateletlike habit. The IR recording of the sample shows a distinct sharp band at 960 cm$^{-1}$. Chemical analysis reveals a molar ratio in the product of Si/Ti=37.7. Alkali metal impurity was only 0.0015% by weight of sodium and 0.0045% by weight of potassium. Based on starting SiO$_2$, the yield of crystalline, calcined product was 90.3%.

Example 5

Describes the use of the titanium zeolite prepared in Comparative Example 1 for the catalytic ammonoximation of cyclohexanone to cyclohexanone oxime.

In a glass pressure vessel, 1.75 g of the calcined titanium zeolite prepared in Example 1 were dissolved together with 10.5 g of cyclohexanone and 16.0 g of aqueous ammonia solution in 25 g of tertbutanol by continuous stirring. The temperature was raised to 80° C., and 18.4 ml of a hydrogen peroxide solution (30% by weight) were metered in over 15 minutes. A reaction starts and was subsequently continued for 5 hours. The cold exit mixture was repeatedly extracted with toluene to remove the organic phase. The products were analyzed by gas chromatography.

It was found that cyclohexanone conversion was 67.8% and the selectivity for the target product cyclohexanone oxime was 61.5%.

Example 6

Describes the novel use of the titanium zeolite prepared in Example 3 for the catalytic ammonoximation of cyclohexanone to cyclohexanone oxime.

In a glass pressure vessel, 4.2 g of the calcined titanium zeolite prepared in Example 3 were dissolved together with 10.5 g of cyclohexanone and 23.4 g of aqueous ammonia solution in 23.4 g of tert-butanol by continuous stirring. The temperature was raised to 80° C., and 18.1 ml of a hydrogen peroxide solution (30% by weight) were metered in over 15 minutes. A reaction starts and was subsequently continued for 5 hours. The cold exit mixture was repeatedly extracted with toluene to remove the organic phase. The products were analyzed by gas chromatography.

It was found that cyclohexanone conversion was 89.4% and the selectivity for the target product cyclohexanone oxime was 94.2%.

We claim:

1. A process for the preparation of essentially alkali-free and amine-free titanium zeolite crystals which have an elongate platelet shape and a diffractogram corresponding to the orthorhombic MFI structure with a characteristic band in the IR spectrum of from 950 to 960 cm$^{-1}$, which comprises:

reacting for crystallization under hydrothermal conditions an aqueous reaction mixture consisting of water, ammonia, SiO$_2$, a tetraalkylammonium halide selected from the group consisting of tetrapropylammonium chloride and tetrapropylammonium bromide, and a peroxotitanate compound dissolved in water or alcohol, in a molar ratio of ammonia/tetraalkylammonium halide of from 3:1 to 200:1 while maintaining a molar ratio of ammonia, used as aqueous solution, to $SiO_2$ of from 10:1 to 1:1, and in a molar ratio of $SiO_2/TiO_2$ of from 10:1 to 1500:1; and subsequently subjecting the product of said hydrothermal crystallization to a heat treatment at from 350° C. to 600° C.

2. A process as claimed in claim 1, wherein the tetraalkylammonium halide is tetra-n-propylammonium bromide.

3. A process as claimed in claim 1, wherein $SiO_2$ is added to the crystallization mixture in a ratio of $SiO_2/H_2O$ of from 0.07:1 to 0.025:1.

4. A process as claimed in claim 1, wherein the tetraalkylammonium halide is a dissolved tetra-n-propylammonium halide used in a molar ratio of said halide/$SiO_2$ within the range of from 0.042:1 to 0.2:1.

5. A process as claimed in claim 4, wherein tetra-n-propylammonium bromide is used in a molar ratio of said bromide/$SiO_2$ within the range of from 0.05:1 to 0.15:1.

6. A process as claimed in claim 1, wherein the hydrothermal crystallization is carried out at from 100° C. to 250° C. and the heat treatment is carried out at from 400° C. to 550° C.

7. A process as claimed in claim 1, wherein the hydrothermal crystallization is carried out at from 120° C. to 200° C. and the heat treatment is carried out at from 4.50° C. to 500 ° C.

8. The titanium silicate zeolite crystalline product obtained by the process of claim 1, wherein the crystals have a uniform size of from about 8 μm to 50 μm.

* * * * *

UNITED STATES PATENT AND TRADEMARK OFFICE
CERTIFICATE OF CORRECTION

PATENT NO. : 5,401,486
DATED : March 28, 1995
INVENTOR(S) : Mueller et al.

It is certified that error appears in the above-identified patent and that said Letters Patent is hereby corrected as shown below:

Column 8:

Claim 7, line 14, change "4.50°" to --450°--.

Signed and Sealed this

Thirtieth Day of May, 1995

*Attest:*

BRUCE LEHMAN

*Attesting Officer*   *Commissioner of Patents and Trademarks*